United States Patent
Edler et al.

(10) Patent No.: US 10,401,226 B2
(45) Date of Patent: Sep. 3, 2019

(54) METHOD OF SECURING A MODULATION RANGE

(71) Applicant: SICK AG, Waldkirch/Breisgau (DE)

(72) Inventors: Julian Edler, Emmendingen (DE); Thomas Beyer, Freiburg (DE); Samson Frank, Freiburg (DE)

(73) Assignee: SICK AG, Waldkirch/Breisgau (DE)

( * ) Notice: Subject to any disclaimer, the term of this patent is extended or adjusted under 35 U.S.C. 154(b) by 0 days.

(21) Appl. No.: 15/828,512

(22) Filed: Dec. 1, 2017

(65) Prior Publication Data

US 2018/0156664 A1 Jun. 7, 2018

(30) Foreign Application Priority Data

Dec. 5, 2016 (EP) .................................. 16202118

(51) Int. Cl.
*G01N 21/25* (2006.01)
*G01J 3/51* (2006.01)
(Continued)

(52) U.S. Cl.
CPC ................ *G01J 3/51* (2013.01); *G01J 3/027* (2013.01); *G01J 3/10* (2013.01); *G01J 3/18* (2013.01); *G01J 3/42* (2013.01); *G01N 21/274* (2013.01); *G01N 21/39* (2013.01); *G02B 27/10* (2013.01); *G01N 2021/399* (2013.01); *H01S 3/1305* (2013.01)

(58) Field of Classification Search
CPC ........ G01J 3/26; G01J 3/02; G01J 3/51; G01J 9/00; G01N 21/255

USPC ......................................................... 356/416
See application file for complete search history.

(56) References Cited

U.S. PATENT DOCUMENTS 7,952,806 B2 5/2011 Callen et al.
2003/0174743 A1 9/2003 Cliche et al.
(Continued)

FOREIGN PATENT DOCUMENTS

DE    202014105282 U1   2/2016
KR    1020120089321 A   8/2012
WO       2010148263 A1  12/2010

OTHER PUBLICATIONS

European search report dated Jun. 19, 2017 for corresponding application No. EP16202118.
(Continued)

*Primary Examiner* — Md M Rahman
(74) *Attorney, Agent, or Firm* — Nath, Goldberg & Meyer; Jerald L. Meyer; Stanley N. Protigal

(57) ABSTRACT

A method of securing a modulation range of a wavelength-variable radiation source as part of the measurement of an absorption line of a substance comprises: the radiation source being controlled to transmit radiation such that the wavelength of the radiation runs through the modulation range in accordance with a time pattern; the radiation being filtered by means of a filter in whose pass band the absorption line is disposed and which has at least one filter flank whose actual wavelength is within the modulation range; a spectrum of the filtered radiation being determined in that the intensity of the filtered radiation is detected with respect to the time pattern; and a determination being made whether the spectrum has the at least one filter flank.

23 Claims, 2 Drawing Sheets

Figure 1:
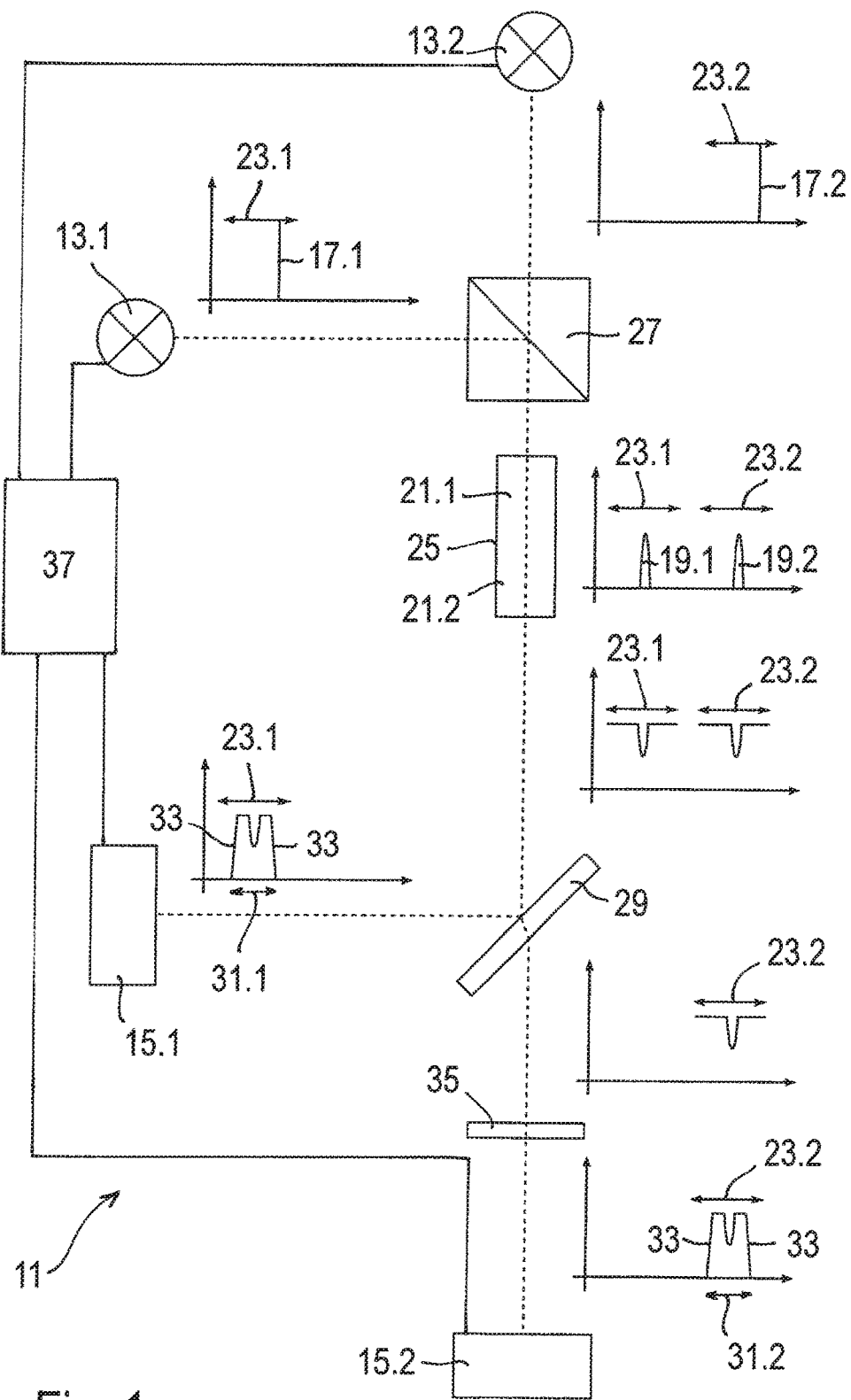

(51) Int. Cl.
  *G02B 27/10* (2006.01)
  *G01J 3/18* (2006.01)
  *G01J 3/10* (2006.01)
  *G01J 3/42* (2006.01)
  *G01N 21/27* (2006.01)
  *G01N 21/39* (2006.01)
  *G01J 3/02* (2006.01)
  *H01S 3/13* (2006.01)

(56) References Cited

U.S. PATENT DOCUMENTS

| | | | |
|---|---|---|---|
| 2005/0018743 A1* | 1/2005 | Volodin | G02B 27/0944 372/102 |
| 2005/0046850 A1* | 3/2005 | Chow | G01B 11/0625 356/430 |
| 2005/0129345 A1* | 6/2005 | Schilling | G02F 1/011 385/8 |
| 2009/0103081 A1* | 4/2009 | Whelan | G01J 3/28 356/243.1 |
| 2010/0292581 A1 | 11/2010 | Howard et al. | |

OTHER PUBLICATIONS

Korean Office Action dated May 15, 2019 corresponding to application No. 10-2017-0165799.

\* cited by examiner

METHOD OF SECURING A MODULATION RANGE

The present invention relates to a method of securing a modulation range of a wavelength-variable radiation source as part of the measurement of an absorption line of a substance, to a method of measuring an absorption line of a substance, and to a spectrometer for measuring an absorption line of a substance.

It is in particular known for the purpose of determining the concentration of a substance to measure an absorption line of the substance, i.e. an absorption spectrum in the range of an absorption characteristic for the substance. Such an absorption line is preferably relatively sharp so that radiation incident onto the substance is only absorbed in a narrow repetency range of some few wave numbers per centimeter, e.g. from approximately 0.5 $cm^{-1}$ to approximately 2 $cm^{-1}$, and, where possible, no absorption takes place in the environment outside this range, with the full width at half maximum of the absorption line being able to amount e.g. to approximately 0.2 $cm^{-1}$. The concentration of the substance can then be determinable with reference to the absorption line, in particular with reference to the extent of the absorption spectrum or with reference to the characteristic values of this extent such as a width, a depth and/or an area of the extent or a derivation of the extent. In this respect even further values may have to be considered for a quantitative measurement, in particular the length of the measurement path along which the radiation passes through the substance, but, for instance, also the pressure and/or the temperature of the respective substance.

The absorption of the radiation in the region of an absorption line can substantially be based on energy transfers that are triggered by radiation having a wavelength corresponding to the energy of the respective transfer, whereby this radiation is then absorbed. If two or more such transfers of a respective substance or also of a plurality of different substances that are examined together are close to one another, in particular overlap, with respect to the absorbed wavelengths, an individual absorption line to be measured (in the sense of the present text) can also comprise the absorption by a plurality of such energy transfers of the one or more examined substances. To this extent, said measurement of an absorption line of a substance also comprises the measurement of optionally superposed absorption spectra that are based on one or more energy transfers of one or more substances.

Radiation can be produced with wavelengths in the range of the absorption line and can be conducted through the substance for the measurement of an absorption line of a substance, for example by means of a spectrometer. In principle, the radiation could simultaneously comprise all the wavelengths in the range of the absorption line or in an even larger range that includes the absorption line. A broadband radiation source would be required for this purpose that generates radiation over the relevant wavelength range with an intensity that is as homogeneous as possible. However, the detection apparatus for detecting the radiation conducted through the substance would then have to be configured to detect the intensity of the radiation in dependence on the wavelength and with a high spectral resolution. Such a wavelength-specific detection apparatus is comparatively complex and/or expensive. Furthermore, in particular a laser that only emits over a narrow band offers the advantage with respect to a broadband radiation source of a high power and of a collimated beam, whereby long optical paths are possible and even high energy losses (e.g. due to dust on the measurement path or non-directed reflections) can still be acceptable.

Alternatively, the absorption line can therefore also be optically sensed in that a wavelength-variable radiation source is used having a very narrow line width, e.g. having a maximum width of approximately 0.001 $cm^{-1}$, preferably of approximately 0.003 $cm^{-1}$. The radiation generated in this manner can then approximately be considered as the radiation of a single wavelength. In particular a tunable diode laser is suitable as the wavelength-variable radiation source having a narrow line width.

The wavelength-variable radiation source can then be controlled to transmit radiation such that the wavelength of the radiation runs through the wavelength range of the absorption line. The absorption of the radiation by the substance is therefore not simultaneously measured for all the wavelengths of the absorption line, but rather consecutively. In this respect, the modulation range, i.e. the wavelength range through which the radiation transmitted by the wavelength-variable radiation source should run is selected such that it completely encompasses the absorption line, with the modulation range preferably being wider than the absorption line so that an environment at both sides of the absorption line is also covered to ensure that the absorption line can be reliably identified. The modulation range can, for example, be at least twice as wide as the absorption line; it is preferably at least three times as wide.

It can generally be sufficient to run through the modulation range continuously from its one end to its other end. Alternatively the modulation range can also be run through a multiple of times, whether in the same direction (e.g. in the manner of saw teeth) or with a change of direction (e.g. in a triangular or sinusoidal form). The speed of the running through also does not have to be constant, but provision can rather be made, for example, to run through a central region of the modulation range that comprises the absorption line more slowly than marginal ranges, for instance to improve the measurement resolution in this range. If a plurality of absorption lines are to be measured simultaneously by means of a plurality of different radiation sources, a time multiplexing can also be provided so that the running through of the modulation range can also be interrupted under certain circumstances. The respective time pattern according to which the modulation range is run through can therefore be selected as very different in dependence on the specific demands.

A spectrum of the radiation conducted through the substance can then also be determined by means of a non-wavelength specific detection apparatus by taking account of the respective time pattern according to which the modulation range is run through. For a respective wavelength can be associated with each measurement time with respect to the time pattern so that an intensity of the radiation detected at a specific time by the detection apparatus can be respectively unambiguously associated with a wavelength via this relationship. A spectrum can in this manner be determined as a wavelength-dependent intensity of the radiation partly absorbed by the substance.

With such a procedure, the wavelength of the radiation is not directly detected, but a conclusion is rather drawn on the wavelength via the time pattern according to which the radiation source is controlled to transmit radiation of different wavelengths. It is therefore important for the correct association of a detected intensity with a wavelength that the radiation source also actually transmits radiation of that wavelength that is predefined by the time pattern of a respective time at this respective time.

Real radiation sources are as a rule, however, not wavelength-stable in the long term. Provision can, for example, be made that the wavelength to be transmitted is predefined for the radiation source by a control current or a control voltage that is varied in accordance with the time pattern. However, the relationship between the respective current or the respective voltage and the actually transmitted wavelength can vary with time. In addition, the respective temperature present additionally also has an effect on the actually transmitted wavelength. Although the radiation source is therefore controlled to transmit radiation such that the wavelength of the radiation runs through the modulation range in accordance with the time pattern, it then actually transmits radiation whose wavelength varies in accordance with a differing pattern so that the modulation range actually being run through can be falsified, in particular drifted to larger or smaller wavelengths.

It is therefore important for a reliable measurement of the absorption line to ensure that the predefined modulation range is also actually run through. It is therefore advantageous to provide measures by means of which the wavelength of the transmitted radiation is checked and the radiation source or its control is adapted as required. Such measures are also known as "line locking".

For example, a radiation source can be checked for deviations of the actually transmitted wavelengths from the wavelengths for whose transmission the radiation source is controlled in that the radiation transmitted by the radiation source is conducted through a reference cuvette having a test substance that has an absorption at a known wavelength within the modulation range, in particular close to the absorption line to be measured, and is preferably present at a comparatively high concentration. A measurement of the test substance can be carried out in this manner substantially corresponding to the measurement of the substance actually to be measured, by which measurement the position of the absorption of the test substance can be determined. If this determined position differs from the known position of the absorption of the test substance to be expected, it can be recognized from this that the measurement of the substance actually to be measured is also defective.

The use of reference cuvettes can, however, be disadvantageous in that they can in turn be defective. The reference cuvette may also not be sufficiently leak tight in the long term under certain circumstances, in particular when the test substance contained in the reference cuvette is a test gas. In addition, condensation and droplet formation can occur that can impair the measurement. The respective test substance can furthermore show aging effects that can influence the absorption. It must finally be taken into account that surface absorption can occur at the reference cuvette itself which can falsify the measurement.

Difficulties can furthermore result if a plurality of radiation sources having different wavelengths or wavelength ranges are used for a simultaneous measurement of different substances. Provision can be made with such a system, in particular with a spectrometer that is modular in that different radiation sources can selectively be arranged thereat, that the optical paths for the respective radiation of the radiation sources can be spatially combined to form a single measurement beam so that the radiation of the different radiation sources passes through a measurement path having the substances to be measured together as a single measurement beam. The measurement beam can then subsequently be split again and can be conducted over different optical paths to different detection apparatus to determine the absorption through the substances and ultimately their concentration. In this respect, the measurement path does not necessarily have to be split into the same beams from which it was previously formed. Provision can rather also be made that the radiation of different radiation sources is conducted to the same detection apparatus, with it then being possible to distinguish between the different radiation sources by multiplexing or with reference to different modulation frequencies of the radiation.

If a plurality of radiation sources are used in such a manner or in a comparable manner, it may be necessary to ensure separately in each case for a plurality of radiation sources, in particular for each radiation source, that the actually transmitted wavelength corresponds to the predefined wavelength, in particular that the respective modulation range the transmitted radiation runs through does not differ from the modulation range to be run through.

Just as many reference cuvettes can generally be provided for this purpose as radiation sources are used for the respective measurement. Each reference cuvette can then have a test substance suitable for the checking of the modulation range of a respective other radiation source. An increased manufacturing and maintenance effort, however, results due to the large number of reference cuvettes. In addition, where the reference cuvettes can be provided is not unproblematic, in particular when the spectrometer is to be of a modular design so that, depending on the application, different radiation sources each having different wavelength ranges can be used at the spectrometer.

Provision can be made, for example, that the measurement beam to which the radiation of all the respective radiation sources is combined is conducted through one or more reference cuvettes. For this purpose, in particular a portion of the measurement path can be branched off as a kind of line-locking channel so that, for instance, a separate line-locking module can be provided for modular use at the respective spectrometer.

If a single reference cuvette is used in this process, it has to respectively contain a test substance for each wavelength range of the respective radiation sources. However, this can be problematic with a modular design of the spectrometer. For, on the addition or replacement of a radiation source, it may be necessary to provide a different set of test substances, which would then respectively make an exchange of the total reference cuvettes necessary. In addition, reference cuvettes would have to be kept in store for a large number of different combinations of radiation sources.

Alternatively to the use of a single reference cuvette, a plurality of reference cuvettes can therefore also be provided in series in the line-locking channel and contain a respective different test substance. With such a configuration, the respective reference cuvettes to be used can then be selected in dependence on the respective radiation sources used at the spectrometer.

Independently of whether a single reference cuvette is used with a plurality of test substances or a plurality of reference substances are used, a separate separating optics would, however, respectively have to be provided to direct the radiation to different detection apparatus, in particular suitable for different wavelengths, after passing through the test substances. Such a separation of the line-locking channel for distributing the radiation that has passed through the reference cuvettes over different detection apparatus, however, as a rule has to be specifically adapted to the different wavelengths combined in the measurement beam so that an adaptation of the beam splitting is also necessary on a change of the radiation sources used.

Alternatively to providing the reference cuvettes in the measurement beam or in a branched off portion of the measurement beam, the respective beam can also first be split into a plurality of part beams, with a respective reference cuvette then being provided in each part beam. It is, however, also not prevented by such a design that, on a change of the wavelengths combined in the measurement beam, an adaptation of a line-locking module configured in this manner would also become necessary.

A further possibility of monitoring the wavelength stability of radiation sources used in a modular manner comprises already branching off respective line-locking channels at the beam combination, that is before the radiation of the different radiation sources are combined to a single measurement beam. The fact can be utilized in this respect that frequently actually unwanted reflections or transmissions that are therefore suppressed as a rule and that can result in losses also occur at beam splitters—that are used as beam combiners for the beam combination. Such otherwise lost portions of a respective beam that can be in the range of a few percent can then be used as a line-locking channel in that they are conducted as a part beam through respective reference cuvettes to detection apparatus.

In such part beams, unlike in the measurement beam or in a branched off portion of the measurement beam, the wavelengths of all the radiation sources are then not combined so that they would first have to be separated. A respective part beam can rather comprise radiation of a single radiation source or only of some few radiation sources that do not necessarily have to be optically separated, but can rather e.g. also be distinguished with reference to time multiplexing or with reference to different test substances that have an absorption of considerably different amounts.

In order already to branch off line-locking channels in a sensible manner on the beam combination and in order to provide in a respective skillful manner reference cuvettes having suitable test substances and cuvettes windows possibly optimized for specific wavelengths, it is important that which wavelengths are provided and in which manner, in particular in which order, they are combined, is fixed beforehand. Such line-locking channels formed on the beam combination are therefore at least not easy to convert when the radiation sources should be able to be selected or replaced in a modular manner as required.

It is an object of the invention to provide a method of securing a modulation range of a wavelength-variable radiation source as part of the measurement of an absorption line of a substance; a method of measuring an absorption line of a substance; and a spectrometer for measuring an absorption line that have a low complexity and can in particular be used flexibly in connection with radiation sources which can be used in a modular manner and of which, where necessary, a plurality are selected and are simultaneously used to measure a plurality of absorption lines of different substances.

The object is respectively satisfied by a method of securing a modulation range; by a method of measuring an absorption line; and by a spectrometer in accordance with the respective independent claim. Preferred embodiments of the invention result from the dependent claims, from the present description and from the drawings.

The respective modulation range of a wavelength-variable radiation source is secured by means of the methods in accordance with the invention and by means of the spectrometer in accordance with the invention. It is to be understood by this that it is ensured that the actual modulation range, i.e. that wavelength range the radiation transmitted by the respective radiation source actually runs through coincides with the predefined modulation range, i.e. with that wavelength range for whose running through the radiation source is controlled. It is therefore a question of avoiding a deviation from the predefined modulation range. Since the respective radiation source can be subject to effects, e.g. aging effects, that can result in such deviations, the modulation range can in particular be secured in that a deviation is made recognizable so that it can be compensated as required. The elimination of the deviation can then e.g. take place by adjusting the radiation source, for instance in that a working point and/or a temperature of the radiation source is readjusted.

To secure the modulation range, the radiation source is first controlled to transmit radiation such that the wavelength of the radiation should run through the modulation range in accordance with a time pattern. In this respect, the radiation source is advantageously controlled to transmit the radiation at least substantially in the same manner as it is also transmitted for a conventional measurement of an absorption line of a respective substance, that is in particular running through the same modulation range in accordance with the same time pattern. Since the running through of the modulation range in a conventional measurement serves for an optical sensing of the absorption line, the modulation range is in this respect advantageously selected such that the absorption line falls in the modulation range.

The transmitted radiation is subsequently filtered by means of a filter. The filter in this respect is in particular wavelength-selective so that the radiation can at least substantially completely pass through the filter in dependence on its respective wavelength or is at least substantially completely prevented therefrom. The filter has at least one filter flank in this process. Such a filter flank represents a transition between a pass band and a cut-off band of the filter, with the filter allowing radiation having a wavelength within a respective pass band of the filter passing and cutting off radiation having a wavelength within a respective cut-off band. Ideally, a respective filter flank corresponds to an abrupt transition between a pass band and a cut-off band of the filter. The transition is, however, gradual as a rule. In this respect, a filter flank can, however, be very steep, e.g. approximately one nanometer or only a few nanometers wide. The wavelength of a filter flank can then e.g. be defined as a center point of its width or as that wavelength at which the radiation is allowed to pass and is cut off by equal amounts. This wavelength is also called the actual wavelength of a respective filter flank in the following since it defines a given and already known physical property of the filter.

The designation as a pass band or as a spectral pass band is in this respect to be understood in each case only with respect to the filter function of the filter, but not to whether the radiation is passed or conducted in another manner through the filter. Depending on the kind of filter, the radiation does not have to pass through the respective filter to be filtered. For a filtering can, for example, also take place in that radiation is reflected at a filter in dependence on the wavelength. In such a case, a respective pass band is defined with respect to the reflection and designates a wavelength range in which radiation is actually not transmitted through the filter, but is rather reflected. The pass band in such a filter corresponds to this extent to a reflective range of the filter. The filtered radiation, i.e. radiation having a wavelength in a cut-off band of the filter, can be absorbed or transmitted at the filter in this process. To this extent, a respective cut-off band of such a filter can correspond to a respective absorption range or transmission range of the filter.

Conversely, with a filter in which the filtering is based on a wavelength-dependent transmission, a respective pass band can correspond to a respective transmission range of the filter. Radiation having a wavelength outside the pass band can be absorbed or reflected at such a filter. To this extent, with such a filter, a respective cut-off band can correspond to a respective absorption range or reflection range of the filter.

The filter can also have a plurality of pass bands and/or a plurality of cut-off bands that are then separated from one another by respective filter flanks so that the filter has a plurality of filter flanks. In this respect, however, the filter has at least one filter flank whose actual wavelength is within the modulation range for whose running through the radiation source is controlled. It is thereby advantageously ensured that some of the radiation transmitted by the radiation source, namely that portion on the pass side of the filter flank, passes the filter and another portion, namely that portion on the cut-off side of the filter flank, does not pass the filter. If a plurality of filter flanks are within the modulation range, mutually disjunctive portions of the filter can also be passed or cut off by the filter with respect to their respective wavelength ranges.

In this respect, the absorption line of the substance to be measured is preferably within, in particular completely within, the spectral pass band of the filter so that the optical sensing of the absorption line is not impeded by the filter. This represents a substantial difference from the use of reference cuvettes that typically have the substance to be measured as the test substance and therefore absorb, that is cut off instead of passing, exactly in the region of the absorption line to be measured.

The radiation filtered in this manner can subsequently be detected. In this respect, the intensity of the filtered radiation is in particular detected with respect to said time pattern. This makes it possible to determine a spectrum of the filtered radiation that describes the intensity of the radiation in dependence on its respective wavelength. The spectrum can, however, be defective to the extent that the relationship between the detected intensity and the wavelength is admittedly established over the time pattern, but it is not certain that the radiation source controlled in accordance with the time pattern actually also transmitted the respective predefined wavelength.

Whether this is the case or whether a deviation is present can now, however, be determined with reference to the effect of the filter, in particular of the filter flank, on the spectrum. For on a transition between a pass band and a cut-off band the filter flank results in a corresponding rise or fall of the detected intensity in the spectrum so that the filter flank can be identified in the spectrum—provided that the spectrum has the filter flank at all. In particular when the filter flank is close to the margin of the modulation range, a drifted modulation range, or one falsified in another manner, can namely be recognizable in that the filter flank is not contained in the falsified modulation range and consequently also not in the spectrum. A simple criterion for securing the modulation range can therefore be the presence of the filter flank in the spectrum.

It can thus be sufficient for the securing of the modulation range to determine whether the spectrum has the at least one filter flank or, with a filter having a plurality of filter flanks within the modulation range, has this plurality of filter flanks. If this applies, the actually run through modulation range corresponds to the predefined modulation range at least within a specific tolerance range. If the spectrum in contrast does not have the filter flank or filter flanks, a modulation range deviating from the specification can be recognized thereby.

A possible further development of the method comprises not only identifying a respective filter flank, but also determining its position and comparing it with the expected position. A measured wavelength of the at least one filter flank in the modulation range can in particular be determined with reference to the spectrum. Since the measured wavelength is in this respect determined with reference to the spectrum, that can be defective as described, this measured wavelength then does not necessarily correspond to the actual wavelength of the filter flank. The presence of a defect can therefore be recognized by a deviation between the measured wavelength and the actual wavelength of the filter flank. The measured wavelength of the at least one filter flank in this advantageous further development of the method is therefore subsequently compared with the actual wavelength of the at least one filter flank.

If in this respect the measured wavelength and the actual wavelength do not coincide, it can be concluded from this that the modulation range that the radiation transmitted by the radiation source has run through also does not coincide with the modulation range for whose running through the radiation source was controlled. If the measured wavelength is in contrast at least substantially, i.e. within a specific tolerance, identical to the actual wavelength of the at least one filter flank it is thereby ensured that the modulation range was actually run through as specified.

The filter is not necessarily fixed to a specific position within the optical path starting from a respective radiation source and incident on a respective detection apparatus. A respective filter can in particular be arranged in one of the manners described further above for reference cuvettes. Provision can, for example, be made that a portion of the measurement beam that should pass through the substances to be measured is branched off and is conducted through the filter. In this respect, a plurality of filters can also be provided, for instance one respective filter for different radiation transmitted by different radiation sources. Provision can also be made that the measurement beam is only again divided into a plurality of part beams after the passing through of the substances to be measured and respective filters are provided in these part beams or in portions branched off therefrom. Alternatively or additionally, one or more filters can furthermore be arranged in the optical paths not yet combined or in the region of the combination of the optical paths.

The different arrangements described above for reference cuvettes can thus generally also be implemented with filters instead of the reference cuvettes, with the filters then making it possible to carry out the method in accordance with the invention. In this respect, a filter not only has the advantage with respect to a reference cuvette of being able to be less prone to aging and less maintenance-heavy and can be integrated better into the measurement without disturbing it. The filter can rather also have a function in the measurement of the absorption line in addition to the securing of the correct modulation range and can therefore provide an expanded use, e.g. in that it contributes to the beam combination or to the beam separation, as will be explained in even more detail in the following.

In general, one filter that has exactly one filter flank in the modulation range can be sufficient to secure the modulation range in the described manner. In accordance with an advantageous embodiment, the filter is, however, configured as a bandpass filter whose pass band is bounded by two filter flanks, with it then being determined whether the spectrum has both filter flanks. In this respect, both filter flanks are preferably within the modulation range, in particular the one filter flank close to the one margin of the modulation range and the other filter flank close to the other margin of the modulation range. Consequently, a part of the modulation range can, so-to-say, be cut out by means of such a bandpass filter, namely that part that corresponds to the pass band of the bandpass filter. The modulation range effectively useful for the measurement is admittedly thereby reduced. But as long as the absorption line lies in the pass band, it does not stand in the way of a measurement of the absorption line.

The advantage of the taking into account of two filter flanks with respect to only one filter flank is then, for example, that independently of the direction of a drift or of another falsification of the modulation range, at least one of the filter flanks is soon no longer covered by the falsified modulation range so that the spectrum no longer has at least this filter flank. The presence of a falsified measurement range can then be recognized by this. As long as the spectrum in contrast has both filter flanks, it is possible to assume a modulation range at least correct within a specific tolerance range so that the modulation range is secured in this manner.

In a similar manner as described above for a filter having at least one filter flank, provision can also be made beyond the mere identification of the filter flanks in the spectrum that respective measured wavelengths of the two filter flanks are determined with reference to the spectrum and that the measured wavelengths are compared with the actual wavelengths of the two filter flanks.

Using a bandpass filter having two filter flanks in the modulation range in this manner as a reference for a deviation of the actual modulation range from the specified modulation range can have the advantage in comparison with a filter having only one filter flank that the degree of the deviation can be determined more reliably, namely e.g. by averaging the two deviations between the measured and the actual wavelengths of the filter flanks, which can be useful for an adjustment of the radiation source under certain circumstances. It can furthermore be avoided by the provision of two filter flanks that the spectrum has no filter flank at all under certain circumstances. For since the absorption line is preferably substantially central within the modulation range, a respective filter flank is rather in a marginal range of the modulation range. If the actually run through modulation range, however, differs greatly from the modulation range actually to be run through, the filter flank can then no longer be covered by the actual modulation range and thus cannot appear at all in the spectrum. Since, however, on the use of a bandpass filter, a respective filter flank is advantageously provided at both sides of the absorption line, the spectrum always has at least one filter flank, at least as long as the absorption line is still within the modulation range, that can then be used for determining the degree of the deviation.

The pass band in this respect preferably has a maximum spectral width of approximately 0.5 cm$^{-1}$, preferably of approximately 1 cm$^{-1}$, in particular of approximately 3 cm$^{-1}$. In this respect, the pass band generally only has to be a little wider than the absorption line of the respective substance to be measured so that the measurement is not impeded by the filter. The pass band is in this respect advantageously only a little wider than the absorption line so that the pass band is completely within the modulation range, that is in turn restricted by the general tenability of the radiation source, and consequently both filter flanks bounding the pass band can be used for a check for a deviation.

In accordance with a further advantageous embodiment, the filter is formed by an optical element, in particular by a beam splitter, that is also used, in addition to the filtering, to combine at least two optical paths spatially. The advantage of such an embodiment is that such an optical element can anyway be provided, namely in particular for the combination of radiation from different radiation sources. Particularly with a spectrometer formed in a modular manner and at which a respective different set of radiation sources is used for a simultaneous measurement of a plurality of substances in dependence on the substances to be measured, a plurality of optical elements can be provided for combining the optical paths starting from the respective radiation sources. In this respect, generally each of these optical elements can also be formed as a filter as part of the described method of securing the modulation range of a respective radiation source.

Whenever two optical paths are combined by means of such an optical element, the wavelength range of the radiation of at least one of the optical paths can be modified by the optical element acting as a filter in this respect so that the respective filter flanks are imparted into the wavelength profile of the radiation so-to-say as markers. When the radiation of all the radiation sources is filtered in this manner, in particular by respective bandpass filters, on the combining of the radiation to a single measurement beam, the measurement beam can as a result comprise radiation that respectively only has wavelengths in a narrow range around a respective absorption line to be measured, with a respective such region being sharply bounded, in particular at both sides, by a respective filter flank. Respective filter flanks are thus available for each absorption line to be measured as a reference by which it can be ensured that the respective modulation range is correctly run through.

In general, the filtering for imparting respective filter flanks as markers into the respective spectrum, however, does not, or at least does not exclusively have to take place on the combination of a plurality of optical paths to one single measurement path. Provision can rather also be made that the radiation is filtered on the division of a measurement beam formed in such a manner into a plurality of part beams directed to different detection apparatus. It can therefore furthermore be advantageous for the filter to be formed by an optical element, in particular by a beam splitter, that is also used in addition to the filtering to spatially split an optical path into at least two optical paths. It may be in particular be useful to use beam splitters suitable as filters for the division when such a splitting of the measurement beam is anyway provided. The radiation directed to a respective detection apparatus then has wavelength ranges that are bounded by respective filter flanks whose measured wavelength can then respectively be compared with their actual wavelength.

In accordance with a preferred embodiment, the filter comprises a volume Bragg grating at which the radiation is reflected for filtering. A volume Bragg grating has a modulation of the refractive index in the substrate that can in particular be produced holographically, e.g. in photosensitive glass as the substrate. The specific design of the volume Bragg grating has the consequence that radiation is only reflected at the volume Bragg grating when the so-called Bragg condition is satisfied, which greatly depends on the respective wavelength of the radiation and on its respective angle of incidence. Radiation is therefore only reflected at a narrow and comparatively sharply bounded wavelength range at a specific angle of incidence for a specific volume Bragg grating. The volume Bragg grating in this respect therefore represents a bandpass filter with respect to the radiation.

Radiation that does not satisfy the Bragg condition with respect to its wavelength and/or its angle of incidence can in contrast be transmitted. The volume Bragg grating can therefore be used to spatially combine two optical paths, namely in that a second beam is reflected in at the volume Bragg grating with respect to a beam transmitted by the volume Bragg grating while satisfying the Bragg condition so that the two beams are superposed. Provided that the reflected beam has wavelengths outside the pass band of the volume Bragg grating, it is necessarily filtered in so doing. At least one filter flank usable as a filter flank can thus be imparted onto the wavelength profile of the reflected beam by using a volume Bragg grating whose pass band (or at least a filter flank) is within the modulation range that is run through by the radiation of the reflected beam.

In a similar manner, a volume Bragg grating can also be used for dividing a beam into two part beams. A volume Bragg grating is used for this purpose, with that portion of the beam being reflected that satisfies the Bragg condition whose wavelength is therefore in the pass band of the volume Bragg grating to this extent. The other portion can be transmitted by the volume Bragg grating. It is generally also possible in this manner to split two beams used for measuring absorption lines disposed close to one another by means of a volume Bragg grating (or also a different optical element that has suitable filter properties) having a filter flank that is disposed between the two absorption lines and is as steep as possible and in so doing simultaneously to bound the respective wavelength range of both beams by the filter flank so that the boundary that is as sharp as possible can be used for the securing of the modulation range of the respective radiation source.

In accordance with an advantageous embodiment, the method furthermore comprises a warning signal being output and/or the radiation source being adjusted until the spectrum has the at least one filter flank or both filter flanks when it is determined that the spectrum does not have the at least one filter flank or the two filter flanks of the filter configured as a bandpass filter. The adjustment of the radiation source can comprise, for example, a working point and/or a temperature of the radiation source being readjusted.

As already mentioned further above, the determination of whether the spectrum has a respective filter flank can additionally comprise a determination being made whether the spectrum also has the respective filter flank at the wavelength to be expected, namely at the actual wavelength of the respective filter flank. For this purpose, the determination can comprise a measured wavelength of the respective filter flank being determined with reference to the spectrum and the measured wavelength of the respective filter flank being compared with the actual wavelength of the respective filter flank. With a filter configured as a bandpass filter, this can in particular comprise respective measured wavelengths of the two filter flanks bounding the pass band of the filter being determined with reference to the spectrum and the measured wavelengths of the two filter flanks being compared with the actual wavelengths of the two filter flanks.

Such a comparison of a measured wavelength with an actual wavelength of a respective filter flank can be limited to determining whether the measured and actual wavelengths of the respective filter flank coincide, in particular at least within a specific tolerance range, or whether a deviation is present. A deviation which may be present can in particular then be taken into account in the result evaluation.

Provision is made in accordance with an advantageous embodiment that, on a deviation of the measured wavelength of a respective filter flank from the actual wavelength of the respective filter flank, the radiation source is adjusted until the measured wavelength of the respective filter flank coincides at least substantially with the actual wavelength of the respective filter flank. The adjustment of the radiation source can in turn in particular comprise a working point and/or a temperature of the radiation source being readjusted.

For example, the wavelength of the wavelength-variable radiation source can be adjustable by a control current or a control voltage so that the radiation source can be controlled to transmit radiation at a wavelength running through the modulation range in accordance with a time pattern in that the control current or the control voltage predefines the time pattern in a corresponding manner. Said working point can then in particular be defined by a specific current or a specific voltage by which the radiation source is controlled to transmit radiation of a specific base wavelength. The current or the voltage that is to be applied to the radiation source for the transmission of the base wavelength can, however, be changed by aging effects or by other effects, in particular drift. The association that has become defective between the current or voltage and the wavelength can then, however, be readjusted with reference to the determined deviation.

It is particularly advantageous in this respect that both the determination of a deviation and the adjustment of the radiation source can generally be automated.

In addition, the adjustment can also so-to-say take place live in the measurement channel in that radiation is repeatedly transmitted in accordance with the time pattern and a respective spectrum is recorded and in so doing the radiation source is readjusted for so long until the filter flank appears in the spectrum at that point that corresponds to its actual wavelength. The adjustment can be carried out simply and reliably by such a procedure.

It can furthermore be advantageous, in particular when no automatic adjustment of the respective radiation source takes place, if a warning signal is output on a deviation of the measured wavelength of a respective filter flank from the actual wavelength of the respective filter flank.

The warning signal can, for example, be visual or acoustic and can be transmitted by the spectrometer at the site of the measurement. It can, however, also be output remotely via suitable communication means. In addition, a warning can also be integrated in the measurement result in that, for example, it is indicated together with an output measured value, e.g. a concentration of a gas to be measured, that this value is probably defective. An adjustment of the radiation source can then be carried out in response to a respective warning signal.

A method configured in accordance with any one of the above embodiments for securing a modulation range of a wavelength-variable radiation source as part of the measurement of an absorption line of a substance can also be integrated into a method of measuring the absorption line of the substance. For provision is also in particular made for measuring an absorption line of a substance that a radiation source is controlled to transmit radiation such that the wavelength of the radiation runs through a modulation range in accordance with a time pattern and that a spectrum of the radiation is determined in that the intensity of the radiation is detected with respect to the time pattern. The additional previous filtering of the radiation does not stand in the way of the measurement of the absorption line here, particularly since the absorption line is in the pass band of the filter. The same spectrum can therefore be used for measuring the absorption line as for the monitoring of the respective radiation source for possible deviations.

A determination is then made, on the one hand, with reference to the same spectrum of the filtered radiation whether the spectrum has a respective filter flank and optionally a measured wavelength of the respective filter flank of the filter is preferably also determined to compare it with the actual wavelength of the respective filter flank and, on the other hand, the absorption line of the substance is determined, with the latter also being able to take place in a generally conventional manner. In this respect, the determination of the absorption line at least takes place when, preferably only when, it is determined that the spectrum comprises the respective filter flank, in particular when the measured wavelength at least substantially coincides with the actual wavelength. It can thus be ensured that the determined absorption line and a concentration of the respective substance that is optionally determined therefrom is not falsified by a defect of the radiation source. If in contrast a deviation is determined, this can advantageously be taken into account.

In accordance with a further development of this method, provision can furthermore be made that finally a concentration of the respective substance is determined from the absorption line. In particular when the time pattern according to which the radiation source is controlled to transmit radiation is correspondingly configured, this can take place in accordance with the method of wavelength modulation spectroscopy, i.e. in accordance with the evaluation methods known therefor. Such an evaluation, for example, then comprises the determination of a signal progression that is derived from the spectrum and that can, for example, at least substantially be a derivation of the spectrum e.g. a so-called 2f signal. Characteristic values such as an area or a width from which the concentration can be derived can then be determined from such a signal progression. Alternatively to wavelength modulation spectroscopy, however, methods of direct absorption spectroscopy can also be used, for example, with corresponding evaluation methods. The measurement of the absorption line as such is then not necessarily of prime interest in such embodiments of the method in accordance with the invention, but rather ultimately the determination of the concentration of the respective substance.

Said methods for measuring an absorption line or the concentration of a substance can in particular be carried out by means of a spectrometer. The spectrometer can in particular comprise for this purpose a radiation source for transmitting radiation whose wavelength runs through a modulation range in accordance with a time pattern; a filter for filtering the radiation; a detection apparatus for detecting the intensity of the filtered radiation; and a control and evaluation device for controlling the radiation source and for determining a spectrum from the detected intensity of the filtered radiation with respect to the time pattern. The spectrometer can also comprise a plurality of radiation sources that are in particular modular and can selectively be used in different combinations or can be configured such that such radiation sources can be selectively arranged at the spectrometer. The above-described methods can then be carried out correspondingly in parallel with respect to the respective radiation of the different radiation sources such that a plurality of absorption lines of different substances can be measured simultaneously and in so doing the modulation range of the respective radiation source is also secured.

The invention will be described in the following by way of example with reference to the Figures.

Figure 2:
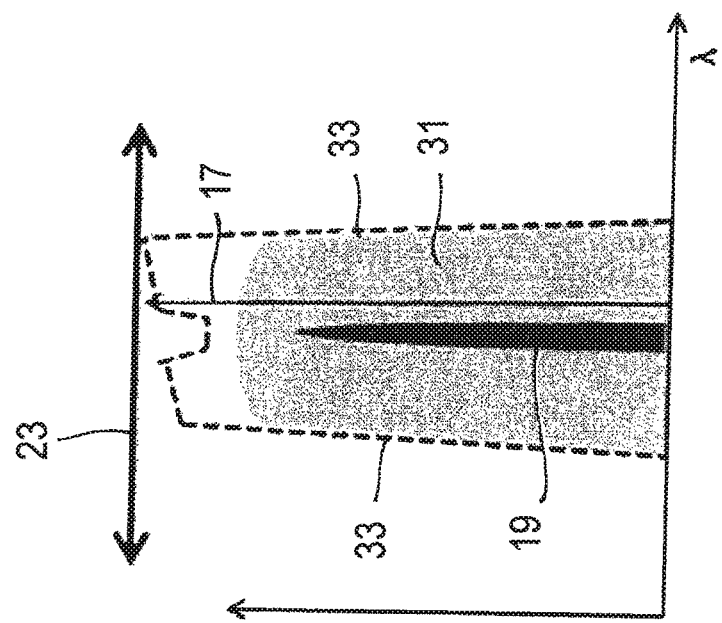
Figure 2:
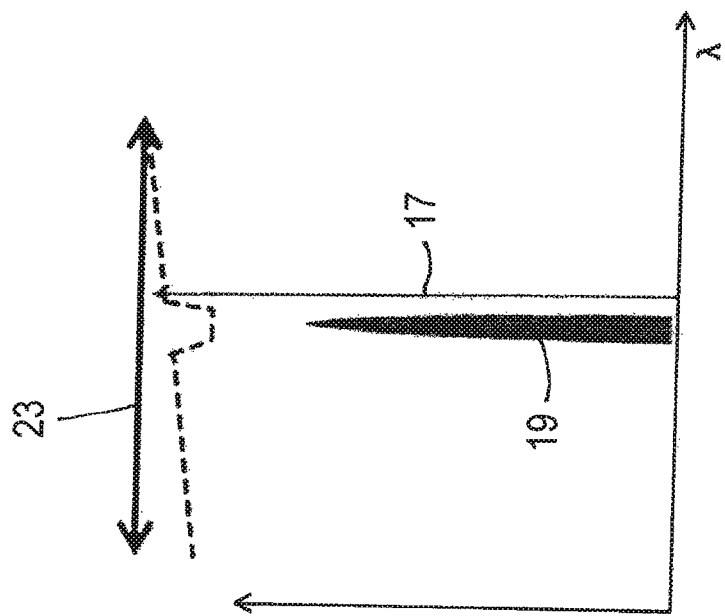

FIG. 1 shows a spectrometer for carrying out a method in accordance with the invention in a schematic representation; and FIG. 2 shows in a schematic representation two exemplary spectra that can be determined in the measurement of an absorption line when the radiation is filtered or not filtered in a manner in accordance with the invention in this respect.

A spectrometer 11 is schematically shown in FIG. 1 that comprises a first radiation source 13.1 and a second radiation source 13.2 as well as a first detection apparatus 15.1 and a second detection apparatus 15.2. The number of radiation sources 13 and of detection apparatus 15 is generally variable here. Just as many detection apparatus 15 as radiation sources 13 in particular do not necessarily have to be provided since the radiation of a plurality of different radiation sources 13 can also be detected by means of a respective detection apparatus 15 and can also be distinguished, for instance using multiplexing.

The two radiation sources 13.1, 13.2 are controllable to generate and transmit radiation that is at least substantially monochromatic in each case, that is at least substantially only has one wavelength or whose respective emission spectrum 17.1, 17.2 has an only narrow line width of narrower than 0.001 cm$^{-1}$, preferably narrower than 0.003 cm$^{-1}$. However, the radiation sources 13.1, 13.2 are wavelength-variable to the extent that the respective transmitted wavelength is variable. The wavelength-variable radiation sources 13.1, 13.2 are in particular tunable diode lasers.

As part of the measurement of respective absorption lines 19.1, 19.2 of substances 21.1, 21.2 to be examined, the radiation sources 13.1, 13.2 are controlled to transmit radiation such that its wavelength runs through a respective modulation range 23.1, 23.2 in accordance with a time pattern. In this respect, the respective modulation range 23.1, 23.2 will at least continuously run through from one end to the other and back again in the example shown. To illustrate this, a respective spectrum is shown, beside the transmitted radiation shown as a broken line, in which the intensity of the radiation (ordinate) is entered schematically against the wavelength (abscissa). The narrow emission spectrum 17.1, 17.2 of the respective radiation source 13.1, 13.2 appears as a vertical line therein. The double arrow shown thereabove indicates the respective modulation range 23.1, 23.2 that is run through by the line. The position of the line within the modulation range 23.1, 23.2 is therefore only a snapshot and not constant.

The spectra shown are purely schematic and only serve for illustration; they are therefore in particular not to scale. The modulation ranges 23.1, 23.2 of the different radiation sources 13.1, 13.2 can therefore also be of different widths, unlike as shown. The modulation ranges 23.1, 23.2 in particular at least differ with respect to their respective positions that are selected such that a respective modulation range 23.1, 23.2 covers a respective absorption line 19.1, 19.2 of the substances to be measured.

The substances 21.1, 21.2 whose absorption lines 19.1, 19.2 are to be measured are located in a measurement cuvette 25 by which a measurement path is defined that is run through for the measurement of the absorption of a measurement beam. The radiation of the two radiation sources 13.1, 13.2 is combined in the measurement beam.

The radiation of the first radiation source 13.1 and the radiation of the second radiation source 13.2 are spatially combined, in particular at least partly superposed, by means of a beam splitter 27 used as a beam combiner to form the measurement beam. The beam splitter 27 can, for example, be a polarizing beam splitter that makes it possible on a corresponding polarization of the respective radiations also to combine wavelengths of modulation ranges 23.1, 23.2 disposed close to one another for measuring absorption lines 19.1, 19.2 disposed close to one another with high efficiency.

Instead of an extractive measurement using a measurement cuvette 25 in which the substances 21 to be measured are received, a different kind of measurement path can generally also be provided. It is in particular also conceivable that the measurement takes place in situ. The measurement path can, for example, extend through a channel in a so-called cross-duct measurement through which the substances 21, in particular gaseous substances, can be conducted.

In addition to the measurement cuvette 25, the absorption lines 19.1, 19.2 of the two substances 21.1, 21.2 are schematically shown in FIG. 1 together with the modulation ranges 23.1, 23.2 of the two radiation sources 13.1, 13.2. In general, however, more than only two substances 21.1, 21.2 can be contained in the measurement cuvette 25 and their respective absorption lines 19 are to be measured. Correspondingly more radiation sources 13 can be provided at the spectrometer 11 for this purpose. It is additionally generally also possible to measure a plurality of absorption lines 19 by means of a single radiation source 13, for instance in that the modulation range 23 of this radiation source 13 extends over a plurality of absorption lines.

As a result of the absorption by the substances 21.2, 21.2, the intensity of the radiation is reduced after passing through the measurement cuvette 25 in the region of a respective absorption line 19.1, 19.2 The measurement beam then has a spectrum such as is shown schematically at the right beneath the measurement cuvette 25. This spectrum comprises radiation in the range of the two modulation ranges 23.1, 23.2, with the absorption in the region of a respective absorption line 19.1, 19.2 being able to be recognized as an intensity collapse in the spectrum.

The measurement beam is subsequently spatially split into two part beams, with one of the part beams simultaneously being filtered. This takes place by means of a volume Bragg grating 29 that is configured only to reflect radiation that is incident to the volume Bragg grating 29 at the angle shown when its wavelength is in a pass band 31.1 of this reflection, with the pass band 31.1 being covered by the modulation range 23.1 of the first radiation source 13.1 and in turn comprising the absorption line 13.1 of the first substance 21.1. The wavelengths outside said pass band 31.1 are therefore filtered from the reflected radiation by the volume Bragg grating 29. The volume Bragg grating 29 to this extent acts as a bandpass filter having said pass band 31.1 with respect to the reflection.

The radiation can then be detected by means of the detection apparatus 15.1 on which the reflected radiation, filtered in this process, is incident and a spectrum can be determined that is shown schematically next to the detection apparatus 15.1. Filter flanks 33 can then be identified in this spectrum that each mark a transition between the pass band 31.1 and a respective cut-off band of the volume Bragg grating 29 adjacent thereto.

The respective actual wavelength of these filter flanks 33 is fixedly pre-defined by the volume Bragg grating 29. The wavelength of a respective filter flank 33 can, however, only be determined from the spectrum via the relationship between the time of the detection and the wavelength of the respective radiation source 13.1 at least supposedly transmitted at this time, that is with reference to said time pattern. However, the wavelength actually transmitted by a respective radiation source 13.1, 13.2 at a respective time can differ from the wavelength for whose transmission the radiation source 13.1, 13.2 was controlled. Such a difference can be recognized in that then the measured wavelength of a respective filter flank 33 that is determined with reference to the spectrum also differs from the actual wavelength of the filter flank 33.

The filter flanks 33 are imparted so-to-say as reference markings on the measured spectrum of a respective absorption line 19 by the filtering of the radiation so that a check can simultaneously also be made with reference to the same spectrum that is used for measuring the absorption line by a simple comparison of the measured wavelength of a respective filter flank 22 with the actual wavelength of the filter flank 33 as to whether there is a deviation at the radiation source 13 that has resulted in a distortion or displacement of the modulation range 23.

In a similar manner, the second part beam that arises by the beam splitting at the volume Bragg grating 29 and is not reflected, but rather transmitted, at the volume Bragg grating 29 can also be filtered to ensure that the modulation range 23.2 of the second radiation source 13.2 also has no difference. For this purpose, a narrow-band bandpass filter 35 can be provided that is passed through by the second part beam and whose pass band 31.2 is covered, on the one hand, by the modulation range 23.2 of the second radiation sources 13.2 and, on the other hand, comprises the absorption line 19.2 of the further substance 21.2 to be measured. In this manner, the spectrum determined by means of the second detection apparatus 15.2 also has two filter flanks 33 bounding the pass band 31.2 whose respective measured wavelength can be determined with reference to the spectrum and can be compared with the respective actual wavelength of the filter flanks 33.

The spectrometer additionally has a control and evaluation device 37 for controlling the radiation sources 13.1, 13.2 and for evaluating the data detected by means of the detection apparatus 15.1, 15.2, in particular for a specific determination of respective spectra, for determining wavelengths of respective filter flanks with reference to the spectra and/or for determining the concentrations of respective substances with reference to the absorption lines in the spectra. The comparison of the measured wavelengths of the filter flanks 33 with their actual wavelengths can in particular also take place in this control and evaluation unit 37. If a deviation is present, the control and evaluation device can subsequently preferably adapt the control of the radiation sources 13.1, 13.2 such that the deviation is actually compensated.

Two spectra are shown in FIG. 2 for illustrating the effect of the filtering of the radiation in accordance with the invention such as can be determined on the measurement of an absorption line 19 of a respective substance 21 to be examined. The two spectra are each shown as a broken line. In addition, the absorption line 19 and (as a double arrow) the modulation range 23 the wavelength of the transmitted radiation runs through are respectively shown. In addition, the emission spectrum 17 of the respective radiation source 13 is shown as a vertical line that actually has no fixed position, but rather runs through the modulation region 23, optionally a multiple of times, over its total extent.

Since only radiation having wavelengths within the modulation range 23 is generated, the respective spectrum also extends at most over its extent. The spectrum in this respect has a corresponding depression in the region of the absorption line 19 due to the absorption of the radiation by the respective substance 21. The spectrum otherwise respectively has an at least substantially constant intensity. The intensity can, however, generally also vary at least slightly in dependence on the wavelength, due to dispersion effects, for instance. The intensity can in particular, as shown in FIG. 2, at least substantially continuously increase as the wavelength increases or as the number of waves decreases.

In the spectrum shown at the right in FIG. 2, the radiation was filtered in a manner in accordance with the invention unlike in the spectrum shown at the right. The pass band 31 of the filter used for this purpose is additionally shown in the right spectrum. It can in particular be recognized that the pass band 31 is completely within the modulation range 23 of the respective radiation source 13 and in turn completely comprises the absorption line 19 of the respective substance 21. In addition, for a reliable optical sensing of the absorption line 19, the line width 17 of the radiation source 13 is narrower than the absorption line 19.

As a comparison of the spectrum shown at the right in FIG. 2 with the spectrum shown at the left shows, the filtering of the radiation in accordance with the invention has the consequence that the spectrum has no intensity outside the pass band 31 of the filter. The filter flanks 33 flanking the pass band 31 can be identified in the right spectrum by the steep drop of the measured intensity and can therefore be used as references as to whether the wavelengths determined with reference to the spectrum and other parameters are defective. It is sufficient for this purpose to compare the measured wavelengths of the filter flanks 33 with their known actual wavelengths. It can then be ensured with reference to this comparison that the modulation range 23 the radiation has actually run through coincides with the predefined modulation range 23 for whose running through the radiation source 13 was controlled.

REFERENCE NUMERALS 11 spectrometer
13 radiation source
15 detection apparatus
17 emission spectrum
19 absorption line
21 substance to be measured
23 modulation range
25 measurement cuvette
27 beam splitter
29 volume Bragg grating
31 pass band
33 filter flank
35 bandpass filter
37 control and evaluation device

The invention claimed is:

1. A method of securing a modulation range of a wavelength-variable radiation source as part of the measurement of an absorption line of a substance, the method comprising the steps of:
controlling the radiation source to transmit radiation such that the wavelength of the radiation runs through the modulation range in accordance with a time pattern;
filtering the radiation by means of a filter in whose pass band the absorption line is disposed and which has at least one filter flank whose actual wavelength is within the modulation range; and
determining a spectrum of the filtered radiation in that the intensity of the filtered radiation is detected with respect to the time pattern;
and making a determination whether the spectrum has the at least one filter flank,
wherein the filter is formed by an optical element that is also used, in addition to filtering, to spatially combine at least two optical paths, or to spatially split an optical path into at least two optical paths.

2. The method in accordance with claim 1,
wherein the filter is configured as a bandpass filter whose pass band is bounded by two filter flanks;
and wherein a determination is made whether the spectrum has both filter flanks.

3. The method in accordance with claim 2,
wherein the pass band has a maximum spectral width of approximately 0.5 $cm^{-1}$.

4. The method in accordance with claim 2,
wherein the pass band has a maximum spectral width of approximately 1 $cm^{-1}$.

5. The method in accordance with claim 2,
wherein the pass band has a maximum spectral width of approximately 3 $cm^{-1}$.

6. The method in accordance with claim 1,
wherein the filter comprises a volume Bragg grating at which the radiation is reflected for filtering.

7. The method in accordance with claim 1,
wherein a warning signal is output and/or the radiation source is adjusted until the spectrum has the at least one filter flank when it is detected that the spectrum does not have the at least one filter flank.

8. The method in accordance with claim 7,
wherein the filter is configured as a bandpass filter whose pass band is bounded by two filter flanks and a warning signal is output and/or the radiation source is adjusted until the spectrum has both filter flanks when it is detected that the spectrum does not have both filter flanks.

9. The method in accordance with claim 1,
wherein the step of determining whether the spectrum has the at least one filter flank additionally comprises determining a measured wavelength of the at least one filter flank with reference to the spectrum and the measured wavelength of the at least one filter flank being compared with the actual wavelength of the at least one filter flank.

10. The method in accordance with claim 9,
wherein the filter is configured as a bandpass filter whose pass band is bounded by two filter flanks and the step of determining whether the spectrum has the at least one filter flank additionally comprises determining respective measured wavelengths of the two filter flanks with reference to the spectrum and the measured wavelengths of the two filter flanks being compared with the actual wavelengths of the two filter flanks.

11. The method in accordance with claim 9,
wherein, on a deviation of the measured wavelength of the at least one filter flank from the actual wavelength of the at least one filter flank, a warning signal is output and/or the radiation source is adjusted until the measured wavelength of the at least one filter flank at least substantially coincides with the actual wavelength of the at least one filter flank.

12. The method in accordance with claim 11,
wherein the filter is configured as a bandpass filter whose pass band is bounded by two filter flanks; and, on a deviation of the measured wavelength of the two filter flanks from the actual wavelengths of the two filter flanks, a warning signal is output and/or the radiation source is adjusted until the measured wavelengths of the two filter flanks at least substantially coincides with the actual wavelengths of the two filter flanks.

13. A method of measuring an absorption line of a substance using the method of securing a modulation range of a wavelength-variable radiation source in accordance with claim 1,
wherein the method of measuring the absorption line of the substance comprises the step of determining the absorption line of the substance with reference to the spectrum of the filtered radiation when it is determined that the spectrum has the at least one filter flank.

14. The method in accordance with claim 13,
wherein the step of determining the absorption line, further comprises determining with reference to the spectrum of the filtered radiation when a measured wavelength of the at least one filter flank determined with reference to the spectrum at least substantially coincides with the actual wavelength of the at least one filter flank.

15. The method in accordance with claim 13,
wherein a concentration of the substance is determined from the absorption line.

16. The method in accordance with claim 15,
wherein the concentration of the substance is determined from the absorption line in accordance with the method of wavelength modulation spectroscopy or of direct absorption spectroscopy.

17. A method of measuring an absorption line of a substance using the method of securing a modulation range of a wavelength-variable radiation source in accordance with claim 1,
wherein the filter is configured as a bandpass filter whose pass band is bounded by two filter flanks;
and wherein the absorption line of the substance is additionally determined with reference to the spectrum of the filtered radiation when it is detected that the spectrum has both filter flanks.

18. The method in accordance with claim 17,
wherein the step of determining the absorption line, further comprises determining with reference to the spectrum of the filtered radiation when respective measured wavelengths of the two filter flanks determined with reference to the spectrum at least substantially coincide with the actual wavelengths of the two filter flanks.

19. The method in accordance with claim 17,
wherein a concentration of the substance is determined from the absorption line.

20. The method in accordance with claim 19,
wherein the concentration of the substance is determined from the absorption line in accordance with the method of wavelength modulation spectroscopy or of direct absorption spectroscopy.

21. A spectrometer for measuring an absorption line of a substance,
the spectrometer comprising:
a radiation source for transmitting radiation whose wavelength runs through a modulation range in accordance with a time pattern;
a filter for filtering the radiation;
a detection apparatus for detecting the intensity of the filtered radiation; and a control and evaluation device for controlling the radiation source and for determining a spectrum from the detected intensity of the filtered radiation with respect to the time pattern, wherein the spectrometer is configured to carry out a method of measuring an absorption line of a substance, wherein the method comprises the carrying out of a method of claim 1.

22. The spectrometer in accordance with claim 21,
wherein, in the method of measuring an absorption line of a substance comprises the step of determining the absorption line of the substance with reference to the spectrum of the filtered radiation when it is determined that the spectrum has the at least one filter flank.

23. The spectrometer in accordance with claim 21,
wherein the filter is configured as a bandpass filter whose pass band is bounded by two filter flanks;
and wherein a determination is made whether the spectrum has both filter flanks.

* * * * *